United States Patent [19]

Küfner-Mühl et al.

[11] Patent Number: 5,675,005
[45] Date of Patent: Oct. 7, 1997

[54] PROCESS FOR PREPARING XANTHINE DERIVATIVES, IN PARTICULAR 1,3-DIPROPYL-8-(3-OXOCYCLOPENTYL)-XANTHINE

[75] Inventors: Ulrike Küfner-Mühl, Ingelheim am Rhein; Sven Lüttke, Ockenheim, both of Germany

[73] Assignee: Boehringer Ingelheim KG, Ingelheim am Rhein, Germany

[21] Appl. No.: 373,324

[22] PCT Filed: May 18, 1994

[86] PCT No.: PCT/EP94/01611

§ 371 Date: Mar. 7, 1995

§ 102(e) Date: Mar. 7, 1995

[87] PCT Pub. No.: WO94/26743

PCT Pub. Date: Nov. 24, 1994

[30] Foreign Application Priority Data

May 18, 1993 [DE] Germany ............ 43 16 576.1

[51] Int. Cl.$^6$ ............ C07D 473/06; C07D 473/08; C07D 405/12; C07D 473/04
[52] U.S. Cl. ............ 544/271; 544/267; 544/268; 544/272; 544/273; 544/311; 549/333
[58] Field of Search ............ 544/267, 268, 544/271, 272, 273

[56] References Cited

U.S. PATENT DOCUMENTS 4,755,517  7/1988  Bruns ............ 574/263

FOREIGN PATENT DOCUMENTS

| | | |
|---|---|---|
| 269841 | 6/1988 | European Pat. Off. |
| 374808 | 6/1990 | European Pat. Off. |
| 386675 | 9/1990 | European Pat. Off. |
| 541120 | 5/1993 | European Pat. Off. |
| 552712 | 7/1993 | European Pat. Off. |
| 560354 | 9/1993 | European Pat. Off. |
| 2091249 | 7/1982 | United Kingdom . |
| 92-00297 | 9/1992 | WIPO . |
| 94-03456 | 2/1994 | WIPO . |
| 94-26743 | 11/1994 | WIPO . |

OTHER PUBLICATIONS

Coelho, Tet Letters 30, 565 (1989).
Venkatachalam, Tet. Letters 27, 4111 (1986).
Nguyen, Tetrahedron 43, 527 (1987).
Horiguchi, *J.A.C.S.* 111, 6257 (1989).

*Primary Examiner*—Mark L. Berch
*Attorney, Agent, or Firm*—Robert P. Raymond; Wendy E. Rieder; Alan R. Stempel

[57] ABSTRACT

This invention relates to a process for preparing xanthine derivatives of formula I:

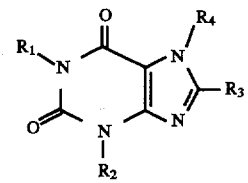

characterized in that a uracil derivative of formula A or B

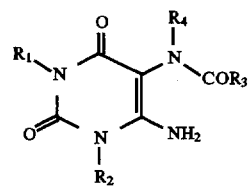

or

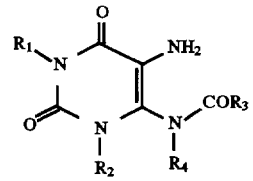

is dissolved in a suitable organic-aqueous solvent and cyclized in the presence of LiOH.

6 Claims, No Drawings

PROCESS FOR PREPARING XANTHINE DERIVATIVES, IN PARTICULAR 1,3-DIPROPYL-8-(3-OXOCYCLOPENTYL)-XANTHINE

The present invention relates to an improved process for preparing xanthine derivatives substituted in the 8-position.

Xanthine derivatives have valuable pharmacological properties as adenosine antagonists. Synthesis processes which enable xanthine derivatives to be prepared in chemically and optically high yields are of particular interest. Xanthine derivatives are usually synthesised by a ring-closure reaction of the correspondingly substituted aminouracils under alkaline conditions—such as for example aqueous sodium hydroxide solution—at elevated temperatures. In many cases at least partial racemisation takes place under these reaction conditions.

It has been shown, surprisingly, that considerably improved yields and higher product quality is obtained if cyclisation of the amido-substituted aminouracils is carried out in an aqueous organic solvent using lithium hydroxide as a base.

The process of the invention is particularly suitable for preparing xanthine derivatives of the general formula

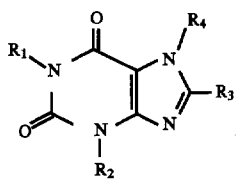

I wherein $R_1$ denotes hydrogen, $C_1$-$C_6$ alkyl, preferably $C_3$-alkyl, in particular n-propyl, $C_3$-$C_6$ alkenyl, preferably allyl or $C_3$-$C_6$ alkynyl;

$R_2$ denotes hydrogen, a $C_1$-$C_8$ alkyl, preferably $C_1$-$C_3$ alkyl, in particular n-propyl, $C_3$-$C_8$ alkenyl or $C_3$-$C_8$ alkynyl group, or a $C_1$-$C_8$ alkyl, preferably $C_1$-$C_8$, in particular $C_3$-alkyl, $C_3$-$C_8$ alkenyl or $C_3$-$C_8$ alkynyl group, which carries one of the following groups:

—$CH_2NR_6R_7$, OH (multiple substitution also possible), —$OR_8$, —$NR_6R_7$, —$NHCOR_8$, —$NHCONR_6R_7$, halogen, —$OCH_2COOH$, —$SO_2R_5$, —S—$R_5$, —NHCONH phenyl, —$OCH_2CH_2OH$, —$OCH_2$—$CH_2$—$NR_6R_7$, —$SO_2$—$CH_2$—$CH_2$—OH, —$OCH_2CH_2OR_8$, —COOH, —$SR_8$, —$SOR_8$, —$SO_2R_8$, —$SO_3H$, —$SO_2NR_6R_7$, —CH=NOH, —$COR_9$, —CH(OH)$R_9$, —$CH(OR_8)_2$, —CH=CH—$R_{10}$,

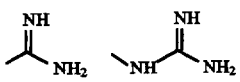

1,3-dioxolane or 1,3-dioxane optionally mono- or poly-substituted—preferably mono—by methyl;

$R_2$ denotes phenyl-$C_1$-$C_3$-alkylene, preferably phenyl-$C_1$-$C_4$-alkylene, phenyl-$C_2$-$C_6$-alkenylene or phenyl-$C_2$-$C_6$-alkynylene, the phenyl ring being optionally substituted either directly or via an alkylene group having 1 to 4 C atoms, by one or more, preferably one, of the following groups, —$C_1$-$C_3$-alkyl, —$CH_2NR_6R_7$, —$NO_2$, —OH, —$OR_8$, —$CH_2$—NH—$SO_2$—$R_8$, —$NHCONR_6R_7$, halogen, —$OCH_2COOH$, —$SO_2R_5$, —$OCH_2CH_2OH$, —$OCH_2$—$CH_2$—$NR_6R_7$, —$OCH_2CH_2OR_8$, —COOH, —$CF_3$, cyclopropyl, —$CH_2OH$, —$CH_2OR_8$, —$SR_8$, —$SOR_8$, —$SO_2R_8$, —$SO_3H$, —$SO_2NR_6R_7$, —$COR_9$, —CH(OH)$R_9$, —$CH(OR_8)_2$, —CH=CH—$R_{10}$,

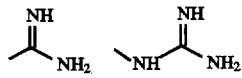

1,3-dioxolane or 1,3-dioxane optionally mono- or poly-substituted by methyl;

$R_2$ denotes $C_3$-$C_7$-cycloalkyl-$C_1$-$C_6$-alkylene,
$C_3$-$C_7$-cycloalkyl-$C_2$-$C_6$-alkenylene,
$C_3$-$C_7$-cycloalkyl-$C_2$-$C_6$-alkinylene, the cycloalkyl group being optionally substituted either directly or via an alkylene group having 1 to 4 C atoms, by —CN, —$CH_2NR_6R_7$, =O, —OH, —$OR_8$, —$NR_6R_7$, halogen, —$OCH_2COOH$, —$SO_2R_5$, —$OCH_2CH_2OH$, —$OCH_2$—$CH_2$—$NR_6R_7$, —$OCH_2CH_2OR_8$, —COOH, —$CH_2OH$, —$CH_2OR_8$, —$SR_8$, —$SOR_8$, —$SO_2R_8$, —$SO_3H$, —$SO_2NR_6R_7$, —$COR_9$, —CH(OH) $R_9$, —$CH(OR_8)_2$, —CH=CH—$R_{10}$,

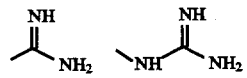

1,3-dioxolane or 1,3-dioxane optionally mono- or poly-substituted by methyl;

$R_2$ denotes a group of the formula
A-$C_1$-$C_6$-alkylene,
A-$C_2$-$C_6$-alkenylene,
A-$C_2$-$C_6$-alkynylene, wherein A is a C-linked or N-linked 5-membered or 6-membered heterocyclic ring containing nitrogen, oxygen or sulphur as hetero atoms, and which may be optionally mono or poly-substituted by $C_1$-$C_4$ alkyl, halogen, —$OR_8$, —$NO_2$, —$NH_2$, —$CH_2NR_6R_7$, —OH, =O, a ketal, —COOH, —$SO_3H$, —$COR_9$, —$SO_2$—$R_8$, or

$R_3$ denotes an optionally substituted C-linked saturated or unsaturated five, six or seven-membered heterocyclic ring containing one or more hetero atoms selected from the group oxygen or sulphur, $R_3$ denotes a $C_4$ to $C_8$ cycloalkene, which may be substituted by $C_2$ to $C_4$ alkenyl, $R_3$ denotes a $C_4$ to $C_8$, preferably $C_5$ and $C_6$-cycloalkanone, or a $C_4$ to $C_8$, preferably $C_5$ and $C_6$-cycloalkanol, which may be substituted in the α-position by $C_2$ to $C_6$, preferably $C_2$ to $C_4$-alkenyl, $C_2$ to $C_6$-, preferably $C_2$ to $C_4$-alkynyl, optionally substituted benzyl, $CH_2OR_4$, $CH_2COOH$, $R_3$ denotes a $C_3$ to $C_8$, preferably $C_5$ or $C_6$-cycloalkane which is optionally substituted by $C_1$ to $C_6$, preferably $C_1$ to $C_4$-alkyl, =$CH_2$, —$OR_4$, —$OR_7$, —$(CH_2)_1$—COOH, —$(CH_2)_1$—$NR_4R_4$ ($R_4$ same or different), —$(CH_2)_1$—$OR_4$, —$(CH_2)_1$—$OR_7$, wherein 1 denotes one of the numbers 0, 1, 2, 3 or 4, or a group =CAH— wherein A may denote COOH, CH=CH—COOH, CH₂OR₄ or CH₂OR₇, or the cycloalkane is substituted by C₁ to C₆, preferably C₁ to C₄ alkyl, vinyl, allyl, optionally substituted phenyl, optionally substituted C₁-C₄ alkylphenyl, and carries as a second substituent a hydroxyl group in a geminal position to the first substituent;

R₃ denotes a ketal of the general formula

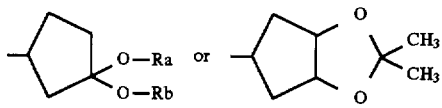

wherein

Ra denotes C₁-C₄ alkyl, and

Rb denotes C₁-C₄ alkyl, or

Ra and Rb together form a C₂ or C₃ alkylene bridge, which may be optionally mono- or di-substituted by C₁-C₅ alkyl:

R₃ denotes an optionally substituted group of the formula

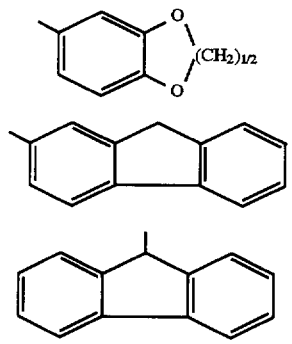

R₃ denotes a group of the formula

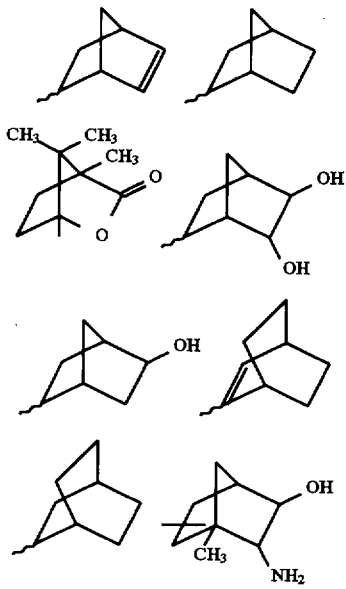

an optionally substituted adamantane;

R₃ denotes C₃-C₇-cycloalkyl, preferably cyclopentyl, which is optionally substituted by =O, —OH, —OR₈, or R₃ denotes phenyl, which is optionally substituted by —OH, halogen, —OR₈, C₁-C₄-alkyl, preferably —CH₃, —NH₂, —COOH, —SO₃H, —COOH, —OCH₂COOH, or R₃ denotes a norbornane, norbornene, a C₃-C₆ dicycloalkylmethyl, adamantane or noradamantane group;

R₃ denotes —CH=CH-phenyl, wherein the phenyl ring is mono- or poly-substituted by methoxy, hydroxy or halogen;

R₃ denotes a [3.3.0]-bicyclooctan-; a [3.3.0]-bicyclooctan-2-yl,

R₃ denotes a C-linked piperidine or furan;

R₄ denotes hydrogen, methyl or benzyl, wherein the benzyl group may be substituted by 1 to 3 methoxy groups;

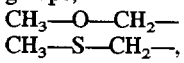

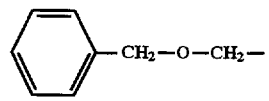

or, —CH₂—CH=CH₂;

R₅ denotes C₁-C₄ alkyl, which is optionally substituted by OH, NH₂ or NR₆R₇, preferably —CH₂—CH₂—OH, —CH₂—CH₂—CH₂—OH;

R₆ denotes hydrogen, an optionally substituted cycloalkyl group having 3 to 6 carbon atoms, a branched or unbranched alkyl, alkenyl or alkynyl group having up to 10 carbon atoms, which may be optionally substituted by hydroxy, phenyl, substituted phenyl, amino, substituted amino, C₁ to C₈, preferably C₁ to C₄-alkoxy;

R₇ denotes hydrogen, an optionally substituted cycloalkyl group having 3 to 6 carbon atoms, a branched or unbranched alkyl, alkenyl or alkynyl group having up to 10 carbon atoms, which may be optionally substituted by hydroxy, phenyl, substituted phenyl, amino, substituted amino, C₁ to C₈-alkoxy;

or

R₆ and R₇ together with the nitrogen atom form a saturated or unsaturated 5 or 6-ring, which may contain nitrogen, oxygen or sulphur as hetero atoms, wherein the heterocyclic ring may be substituted by a branched or unbranched alkyl group having 1 to 4 carbon atoms, or may carry one of the following groups;

—(CH₂)ₙ—NH₂, =O, a ketal, —(CH₂)ₙNH—C₁-C₄-alkyl, —(CH₂)ₙ—N(C₁-C₈alkyl)₂, halogen, —OR₈, —NO₂, —NH₂, —CH₂NR₆R₇, —OH, —COOH, —SO₃H, —SO₂—R₈, R₈ denotes hydrogen, C₁-C₄-alkyl, C₂-C₄-alkenyl, C₂-C₄-alkynyl, benzyl or phenyl group, which is optionally mono- or poly-substituted by OCH₃;

R₉ denotes C₁-C₄-alkyl, C₂-C₄-alkenyl, C₂-C₄-alkynyl, optionally substituted phenyl, optionally substituted benzyl, C₃-C₆-cycloalkyl;

R₁₀ denotes —COOH, —CH₂OR₈, hydrogen, C₁-C₃-alkyl, optionally substituted phenyl, —CH₂NR₆R₇;

R₁₁ denotes hydrogen, phenyl, substituted phenyl, —CH₃.

Xanthines with the abovementioned substituents are described, for example in International patent application PCT/EP 93/020 77. Reference is expressly made to the groups defined as preferred there and the exemplary embodiments.

Further xanthines, which may be prepared according to the process of the invention, are also described in European patent applications 374 808 (89 123 412), 487 673 (PCT/EP 91 01 131), 560 354 and 541 120, reference is also made here to the contents of the exemplary embodiments.

The process of the invention is shown in the reaction scheme below:

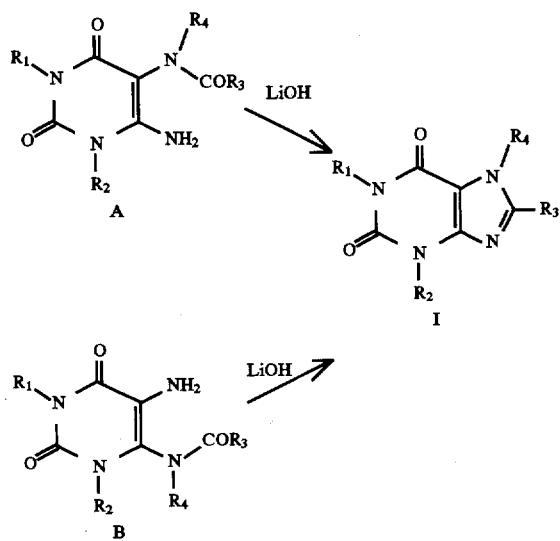

The amides A or B, wherein $R_1$, $R_2$, $R_3$ and $R_4$ have the aforementioned meaning, are dissolved in a suitable hydrophilic solvent or solvent mixture according to the process of the invention. Examples of suitable solvents are water-miscible solvents, such as methanol, ethanol, isopropanol, propanol or tetrahydrofuran. In a particular case it may be necessary to protect functional groups which are sensitive to hydrolysis with a clearable protecting group.

An aqueous solution of lithium hydroxide hydrate is then added—preferably at room temperature, the concentration of LiOH being approximately 0.5 to 2 mole/liter, preferably 1 to 1.5 mole/liter. A 4 to 10 times, preferably 5 to 8 times, excess of lithium hydroxide is used based on the adduct. Cyclisation to give the xanthine is preferably carried out at room temperature, but may also be carried out at elevated temperatures—for example under reflux conditions—to shorten the reaction time. The advantage of the process of the invention lies in the fact that cyclisation takes place under mild reaction conditions even at low temperatures.

Completeness of cyclisation may be monitored, for example by means of thin-layer chromatography. Further working-up is carried out by adjusting the reaction solution to pH 6.5–7, the crystals thus precipitated are isolated according to conventional methods. Alternatively, the reaction solution may be adjusted to pH 4, for example using hydrochloric acid. The organic solvent is then distilled off and the remaining aqueous residue is extracted using an organic solvent and worked up in conventional manner.

The process of the invention is preferred for preparing xanthines of the general formula

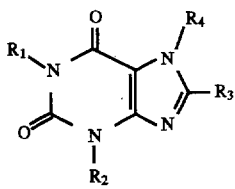

wherein $R_1$ denotes hydrogen, methyl, ethyl, propyl or allyl, preferably n propyl;

$R_2$ denotes hydrogen, methyl, ethyl, propyl or allyl, preferably n propyl;

$R_3$ denotes a cyclopentane, cyclopentanol or cyclopentanone an optionally substituted phenyl $R_3$ denotes an optionally substituted adamantane, norbornane or norbornene, $R_3$ denotes a camphanic acid group or a derivative thereof;

$R_4$ denotes hydrogen or benzyl.

Uracil derivatives of the type A, in which the acid.amide group is arranged in the 5-position of the uracil, are preferred.

An improved process for preparing 1,3-dipropyl-8-(3-oxocyclopentyl)-xanthine is of particular interest.

1,3-Dipropyl-8-(3-oxocyclopentyl)xanthine and both its optically active isomers have valuable pharmacological properties as adenosine antagonists, and are of considerable interest as medicaments for symptomatic treatment of degenerative diseases of the aged, such as for example senile dementia and Alzheimer's disease. The synthesis of the racemate and the optically active isomers is described for the first time in European patent application 374 808.

A maximum yield of about 50% of theory is achieved by the process disclosed there, in some cases it being impossible to avoid purifying the end product chromatographically. It is the object of the present invention to propose a preparation process with high synthetic, and in the case of optically active isomers, with high optical yields, while avoiding chromatographic purification operations.

The process of the invention is sketched in the reaction scheme below.

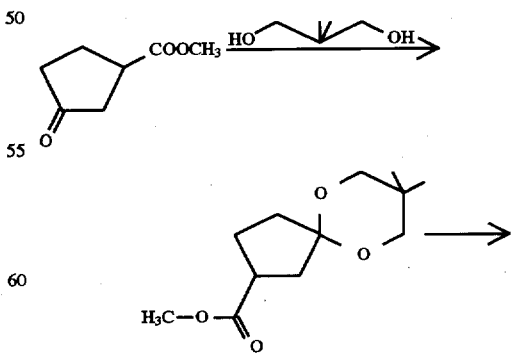

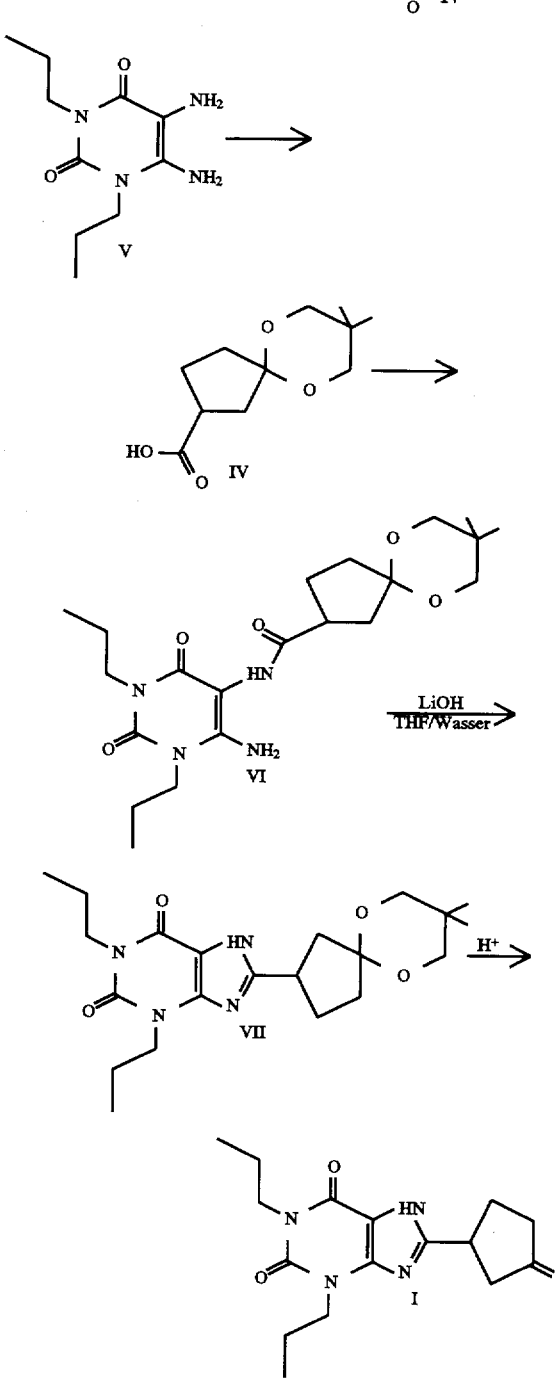

The 2-carboxy-8,8-dimethyl-6,10-dioxaspiro[4,5]decane is obtained starting from optically active alkyl 3-oxocyclopentane carboxylate, preferably methyl 3-oxocyclopentane carboxylate, by reaction with 2,2-dimethylpropane-1,3-diol under acid conditions, such as for example in the presence of pyridinium-4-toluene sulpho-nate. Dealkylation is carried out by hydrolysis using lithium hydroxide hydrate and the free carboxylic acid is obtained.

The 2-carboxy-8,8-dimethyl-6,10-dioxaspiro[4.5] decane—both the racemate and the two enantiomers—are obtained in crystalline form. Although the above-mentioned ketal is the preferred protecting group, other 5-ring and 6-ring ketals may also be used according to the invention as the protecting group.

Hydrolysis of the ester function while preserving optical activity is of decisive importance for the process of the invention. Hydrophilic solvents—water-miscible solvents, such as for example tetrahydrofuran, methanol, ethanol, propanol and isopropanol mixed with water, are suitable solvents. Tetrahydrofuran/$H_2O$ and ethanol/$H_2O$ are preferred. The ketal VII is prepared starting from the carboxylic acid IV by reaction with 5,6-diamino-1,3-dipropyluracil via the amide VI, which is then cyclised to give the xanthine using lithium hydroxide hydrate.

The protecting group is then cleaved using concentrated mineral acid.

The protecting group is cleaved under the usual conditions which are known in the literature, preferred solvent is ethanol/water, preferred mineral acid is concentrated sulphuric acid.

The following examples illustrate the process of the invention.

General Work Guidelines 1.0 mole of adduct is dissolved either in 2,250 ml of ethanol or tetrahydrofuran-water mixture (1,000 ml/3,330 ml) and treated with a solution of 6.1 moles–7.5 moles of lithium hydroxide hydrate in 5,000 ml–6,150 ml of water at room temperature. The reaction mixture is stirred either for 16 hours at room temperature or for 2 hours at room temperature and then for 2.5 hours while boiling under reflux. The completeness of reaction is checked by means of TLC monitoring. The mixture is worked up, either by treatment with 45 g of active charcoal, stirring for 30 minutes at room temperature, filtering off under suction over kieselguhr and washing several times using ethanol/water 1:1, the filtrate is adjusted to pH 6.5–7 using 4N HCl and the precipitated crystals are filtered off under suction, or the reaction mixture is adjusted to pH 4 using 4N HCl, the tetrahydrofuran is distilled off in vacuo, the distillation residue is extracted 3× using 500 ml of methylene chloride each time, the combined organic phases are washed 2× using 350 ml of water each time, dried using magnesium sulphate and evaporated to dryness in vacuo. The product is purified either by recrystallisation using a suitable solvent or by column chromatography over silica gel using a suitable mobile phase.

TABLE 1

| Example | Yield | M.p. |
| --- | --- | --- |
| (1) | 79.6% | 130–132° C. |
| (2) | 86.4% | 172° C. |
| (3) | 19.3% | 251–252° C. |
| (4) | 19.3% | 153–154° C. |
| (5) | 60.1% | 306–307° C. |
| (6) | 81.3% | 298–299° C. |
| (7) | 71.1% | 157–158° C. |
| (8) | 82.7% | 174–176° C. |
| (9) | 57.1% | 194–196° C. |
| (10) | 90.9% | 257–258° C. |
| (11) | 64.0% | >370° C. |
| (12) | 20.4% | 199–200° C. |
| (13) | 57.6% | 172–173° C. |

The 1,3-di-n-propyl-8-(1,3-dioxa-2,2-dimethyl-bicyclo [3.3.0]octan-5-yl)-xanthine (7), the hydrolysis of which using sulphuric acid produces the corresponding 1,3-di-n-propyl-8-(3,4-dihydroxycyclopentanyl)-xanthine, is of particular interest.
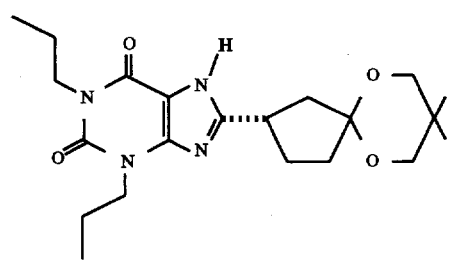
(1)
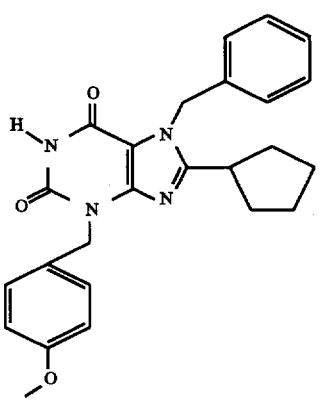
(2)
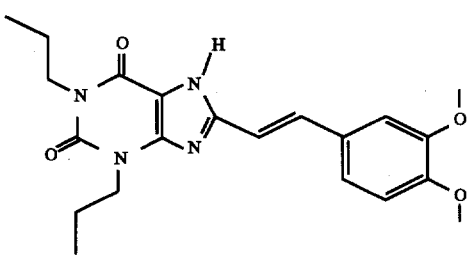
(3)
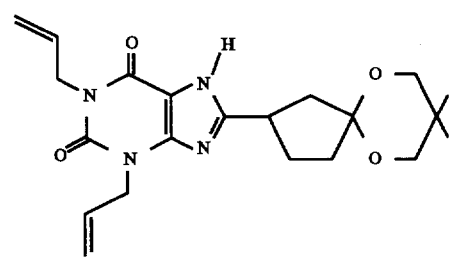
(4)
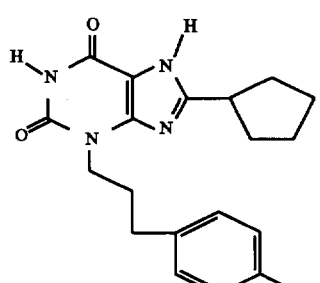
(5)
-continued
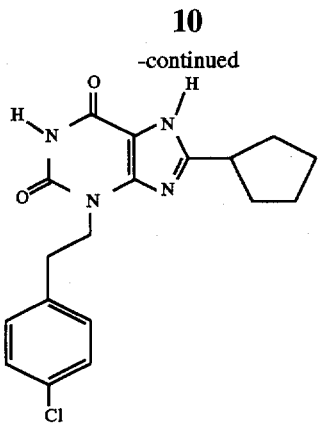
(6)
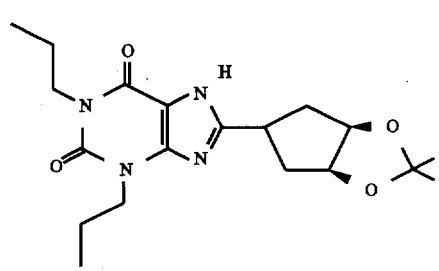
(7)
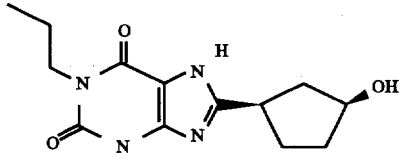
(8)
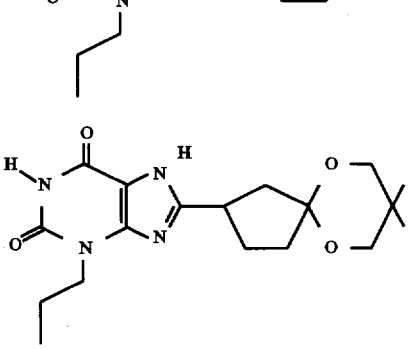
(9)
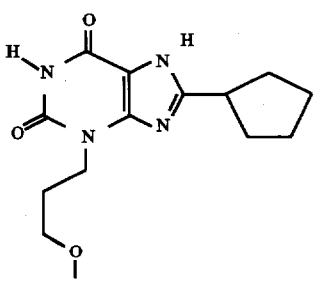
(10)
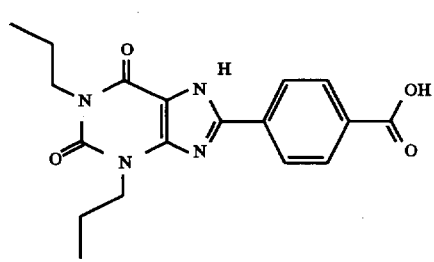
(11)

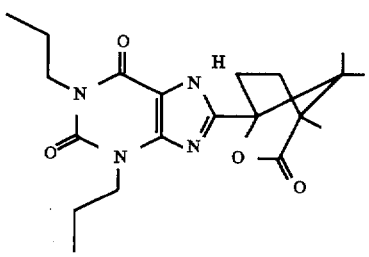

(12)

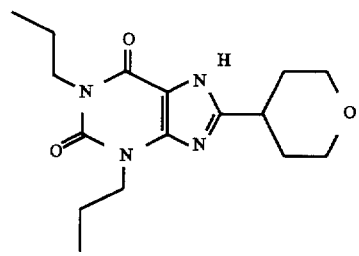

(13)

The following examples illustrate the synthesis of a particularly preferred embodiment. Both the racemic 1,3-dipropyl-8-(3-oxocyclopentyl)xanthine I, the R(+)-1,3-dipropyl-8-(3-oxocyclopentyl)xanthine Ia and also the S(−)-1,3-dipropyl-8-(3-oxocyclopentyl)xanthine Ib, may be prepared under the given reaction conditions, depending on the optical activity of the 3-oxocyclopentane carboxylic acid IIa (OCC) used.

For the preparation of the enantiomers Ia and Ib, care should be taken to ensure that the OCC used should have an optical purity of >99%, since partial racemisation of 1–3% may occur during the course of synthesis (the formation of amide VI and subsequent ring closure are particularly critical).

1. Methyl 3-oxocyclopentane carboxylate: (OCCME)

A solution of 193.8 g (1.51 moles) of 3-oxocyclopentane carboxylic acid in 580 ml of methanol, analytical grade, is treated with 1.8 g (9.5 mmoles) of toluene sulphonic acid hydrate with stirring, then 192.4 g (1.81 moles) of trimethyl orthoformate are added in the course of 10 minutes and the mixture is heated to boiling under reflux. This temperature is maintained for 1 hour. The solution is evaporated in vacuo (i.v.), the residue is treated with 200 ml of $H_2O$, 220 ml of toluene and 1.9 ml of concentrated $H_2SO_4$ and stirred at room temperature for 1 hour. The phases are separated, the aqueous phase is extracted 3× using 50 ml of toluene each time, the combined organic phases are washed 1× using 90 ml of 2.5% strength LiOH solution and 2× using 50 ml of $H_2O$ each time. The organic phase is dried using magnesium sulphate and evaporated in vacuo. The oily residue is fractionally distilled using a water-jet vacuum.

Result: 204.5 g (88.4% of theory) of clear, colourless oil, $bp_{20mbar}$: 110°–112° C., Optical purity>99.8%.

Processes for preparing the R,(+) or S,(−)-3-oxocyclopentane carboxylic acid used as starting compound, are known from the prior art, a preferred process is disclosed in German publication DE-OS 4 140 688.

2. 2-Carboxy-8,8-dimethyl-6,10-dioxaspiro[4,5] decane 72.8 g (0.70 mole) of 2,2-dimethylpropane-1,3-diol and 12.2 g (0.05 mole) of pyridinium-4-toluenesulphonate are added one after another to 40.0 g (0.28 mole) of methyl 3-oxocyclopentane carboxylate OCCME in 560 ml of absolute toluene. The mixture is boiled for 1.5 hours in a water separator; after 30 minutes the solid is dissolved. Approximately 8 ml of $H_2O$ in total are separated out. After cooling, the solution is washed three times using 100 ml of $H_2O$ each time, the toluene phase is dried over $MgSO_4$ and evaporated in vacuo. The oily residue is fractionally distilled in vacuo at 0.6 mbar over a metallised pin tube column 20 cm long.

Result: 51.0 g (79.8% of theory) of colourless oil, $bp_{0.6 mbar}$: 97°–103° C.

When using (R,+)-OCCME (99.6% (R) form): $[\alpha]_D^{20}$=−20.2 (c=1.2; $CH_3OH$)=99% (R) form.

3. 2-Carboxy-8,8-dimethyl-6,10-dioxaspiro[4,5] decane

A solution of 51.0 g (0.23 mole) of 2-carbomethoxy-8,8-dimethyl-6,10-dioxaspiro[4,5]decane in 225 ml of tetrahydrofuran (THF) is added to a suspension of 11.7 g (0.28 mole) of lithium hydroxide hydrate in 1,450 ml of $H_2O$ and the mixture is stirred for 1.5 hours at room temperature. While stirring the pH is adjusted to 7 using about 150 ml of 4N HCl, then the THF is distilled off in vacuo at 40° C. bath temperature. The pH of the aqueous phase is adjusted to pH 4.5 by adding 2N HCl, it is saturated using NaCl and extracted a total of four times using 400 ml of ether. In between a pH of 4.5 must be set again in each case. The combined organic phases are dried over $Na_2SO_4$ and evaporated in vacuo. The residue is dried for one hour at 100° C. in a vacuum drying cabinet. (In the process the substance melts and becomes solid again on cooling.)

Result: 43.1 g (87.5% of theory) of colourless, crystalline solid.

When using (R,+)-OCCME (99.6% (R) form): $[\alpha]_D^{20}$=−15.2 (c=1.32; $CH_3OH$), M.p.: 82° C.

4. Ketal VII 1,3-dipropyl-8-(8,8-dimethyl-6,10-dioxaspiro[4,5]decan-2-yl)-xanthine A: 17.2 g (0.08 mole) of 2-carbomethoxy-8,8-dimethyl-6,10-dioxaspiro[4,5]decane are dissolved in 270 ml of acetonitrile, analytical grade, in an apparatus filled with $N_2$ and heated under a nitrogen atmosphere. While stirring 18.2 g (0.08 mole) of 5,6-diamino-1,3-dipropyluracil, 8.0 g (0.08 mole) of N-methylmorpholine and molecular sieve (0.3 nm) are added at room temperature and the mixture is then cooled to 5° C. A solution of 10.8 g (0.08 mole) of isobutyl chloroformate in 70 ml of acetonitrile, analytical grade, are added dropwise at this temperature in the course of about 45 minutes. The mixture is stirred for 2 hours at 5° C., the colour of the mixture changing from yellow to pink. The batch is treated with 100 ml of $H_2O$ and extracted twice using 200 ml of $CH_2Cl_2$ each time, the combined organic phases are dried over $Na_2SO_4$ and evaporated in vacuo. 37.3 g of yellowish foam are obtained, about 80% strength (about 88% of theory) according to NMR.

The amide decomposes very easily; it should be handled under a protective gas atmosphere and ideally immediately reacted further. Determination of the rotation value or the optical purity is not advisable at this stage.

B: A suspension of 4.6 g (0.11 mole) of lithium hydroxide hydrate in 100 ml of $H_2O$ is treated while stirring with a solution of 10.3 g (0.018 mole) of amide (75% strength) in 40 ml of ethanol. The batch is stirred for 16 hours at room temperature, adjusted to pH 4.5 using 20 ml of 4N HCl and 50 ml of 1N HCl with ice cooling and then the precipitated crystals are filtered off under suction. They are subsequently washed twice using 50 ml of $H_2O$ each time. 7.3 g (100% of theory) of pale yellow crystals are obtained.

When using (R,+)-OCCME (99.6% (R) form): M.p.: 133°–134° C., $[\alpha]_D^{20}$=–21.3 (c=0.47; $CH_3OH$)=98% (R) form.

Cleaving the protecting group 42.7 g (0.11 mole) of ketal VII are dissolved in 200 ml of anhydrous ethanol, analytical grade, and treated with 100 ml of $H_2O$ and 2.8 ml of concentrated $H_2SO_4$. The solution is stirred for 60 minutes at 60° C., it is treated with 600 ml of $H_2O$ and cooled in an ice bath. The precipitated crystals are filtered off under suction, washed using ethanol and dried. Should ketal compound still be present in the crude product, this process has to be repeated. The crude product is recrystallised from three times the amount of ethanol (11.4 g of colourless crystals), the mother liquor is evaporated in vacuo and the residue is recrystallised once again from three times the amount of ethanol (10.5 g of colourless crystals).

A total of 21.9 g (62.5% of theory) of colourless crystals are obtained.

When using (R,+)-OCCME (99.6% (R) form): M.p.: 179.5°–180.5° C., $[\alpha]_D^{20}$=+9.0 (c=0.42; $CH_3OH$)=98.8% (R) form.

We claim:

1. A process for preparing enantiomerically pure 1,3-dipropyl-8-(3-oxooycyclopentyl) xanthine, characterised in that an optically pure compound of formula V:

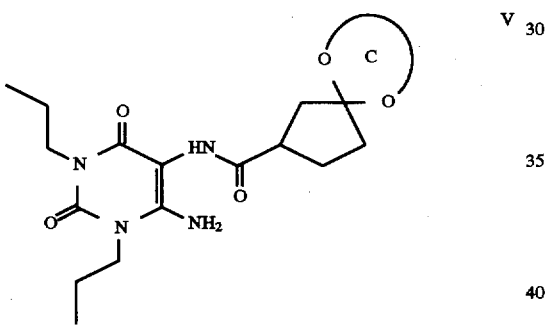

wherein C denotes a ketal protecting group, is cyclised in a suitable hydrophilic solvent in the presence of $LiOH/H_2O$ and the cyclised product is contacted with acid to produce 1,3-dipropyl-8-(3-oxocyclopentyl)xanthine.

2. A process for preparing xanthine derivatives of formula I

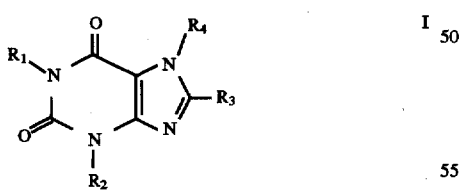

wherein $R_1$ denotes hydrogen, $C_1$–$C_6$-alkyl or $C_3$–$C_6$-alkenyl;

$R_2$ denotes hydrogen, a $C_1$–$C_8$-alkyl, $C_3$–$C_8$-alkenyl or $C_3$–$C_8$ alkynyl group, or a $C_1$–$C_8$-alkyl, $C_3$–$C_8$-alkenyl or $C_3$–$C_8$-alkynyl group, which may carry one of the following groups:

—$CH_2NR_6R_7$, OH (multiple substitution also possible), —$OR_8$, —$NR_6R_7$, —$NHCOR_8$, —$NHCONR_6R_7$, halogen, —$OCH_2COOH$, —$SO_2R_5$, —S—$R_5$, —NHCONH phenyl, —$OCH_2CH_2OH$, —$OCH_2$—$CH_2$—$NR_6R_7$, —$SO_2$—$CH_2$—$CH_2$—OH, —$OCH_2CH_2OR_8$, —COOH, —$SR_8$, —$SOR_8$, —$SO_2R_8$, —$SO_3H$, —$SO_2NR_6R_7$, —CH=NOH, —$COR_9$, —CH(OH)$R_9$, —$CH(OR_8)_2$, —CH=CH—$R_{10}$,

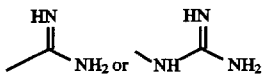

1,3-dioxolane or 1,3-dioxane optionally mono- or poly-substituted with methyl;

$R_2$ denotes phenyl-$C_1$–$C_6$-alkylene, phenyl-$C_2$–$C_6$-alkenylene or phenyl-$C_2$–$C_6$-alkynylene, the phenyl ring being optionally substituted either directly or via an alkylene group having 1 to 4 C atoms, by one or more of the following radicals:

—$C_1$–$C_3$-alkyl, —$CH_2NR_6R_7$, —$NO_2$, —OH, —$OR_8$, —$CH_2$—NH—$SO_2$—$R_8$, —$NHCONR_6R_7$, halogen, —$OCH_2COOH$, —$SO_2R_5$, —$OCH_2CH_2OH$, —$OCH_2$—$CH_2$—$NR_6R_7$, —$OCH_2CH_2OR_8$, —COOH, —$CF_3$, cyclopropyl, —$CH_2OH$, —$CH_2OR_8$, —$SR_8$, —$SOR_8$, —$SO_2R_8$, —$SO_3H$, —$SO_2NR_6R_7$, —$COR_9$, —CH(OH)$R_9$, —$CH(OR_8)_2$, —CH=CH—$R_{10}$,

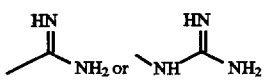

1,3-dioxolane or 1,3-dioxane optionally mono- or poly-substituted by methyl;

$R_2$ denotes $C_3$–$C_7$-cycloalkyl-$C_1$–$C_6$alkylene,
$C_3$–$C_7$-cycloalkyl-$C_2$–$C_6$-alkenylene,
$C_3$–$C_7$-cycloalkyl-$C_2$–$C_6$-alkynylene, the cycloalkyl group being optionally substituted either directly or via an alkylene group having 1 to 4 C atoms, by —CN, —$CH_2NR_6R_7$, =O, —OH, —$OR_8$, —$NR_6R_7$, halogen, —$OCH_2COOH$, —$SO_2R_5$, —$OCH_2CH_2OH$, —$OCH_2$—$CH_2$—$NR_6R_7$, —$OCH_2CH_2OR_8$, —COOH, —$CH_2OH$, —$CH_2OR_8$, —$SR_8$, —$SOR_8$, —$SO_2R_8$, —$SO_3H$, —$SO_2NR_6R_7$, —$COR_9$, —CH(OH)$R_9$, —$CH(OR_8)_2$, —CH=CH—$R_{10}$,

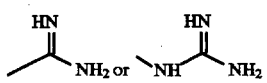

1,3-dioxolane or 1,3-dioxane optionally mono- or poly-substituted by methyl;

$R_2$ denotes a group of the formula

A-$C_{1.1-C6}$-alkylene,
A-$C_2$–$C_6$-alkenylene,
A-$C_2$–$C_6$-alkynylene, wherein A is a C-linked or N-linked 5-membered or 6-membered heterocyclic ring containing one nitrogen, oxygen or sulphur as the hetero atom, and which may be optionally mono- or poly-substituted by $C_1$–$C_4$-alkyl, halogen, —$OR_8$, —$NO_2$, —$NH_2$, —$CH_2NR_6R_7$, —OH, =O, —COOH, —$SO_3H$, —$COR_9$, —$SO_2$—$R_8$, or

$R_3$ denotes a C-linked saturated or unsaturated five, six or seven-membered heterocyclic ring containing one hetero atom selected from the group oxygen or sulphur, or $R_3$ denotes a $C_4$ to $C_8$ cycloalkene, which may be substituted by $C_2$ to $C_4$ alkenyl, or $R_3$ denotes a $C_4$ to $C_8$-cycloalkanone, or a $C_4$ to $C_8$-cycloalkanol, which may be substituted in the α-position by $C_2$ to $C_6$-alkenyl, $C_2$ to $C_6$-alkynyl, benzyl, $CH_2OR_4$, $CH_2COOH$, or $R_3$ denotes a $C_3$ to $C_8$-cycloalkane which is optionally substituted by $C_1$ to $C_6$-alkyl, $=CH_2$, $-OR_4$, $-OR_7$, $-(CH_2)_I-COOH$, $-(CH_2)_I-NR_4R_4$ ($R_4$ same or different), $-(CH_2)_I-OR_4$, $-(CH_2)_I-OR_7$, wherein I denotes one of the numbers 0, 1, 2, 3 or 4, or a group $=CA'H$ wherein A' denotes COOH, $CH=CH-COOH$, $CH_2OR_4$ or $CH_2OR_7$, or the $C_3$ to $C_8$-cycloalkane is substituted by $C_1$ to $C_6$ alkyl, vinyl, allyl, phenyl, $C_1$-$C_4$-alkylphenyl, and carries as a second substituent a hydroxyl group in a geminal position to the first substituent; or $R_3$ denotes a ketal of formula

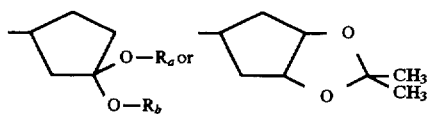

wherein

Ra denotes $C_1$-$C_4$ alkyl, and

Rb denotes $C_1$-$C_4$ alkyl, or

Ra and Rb together form a $C_2$ or $C_3$-alkylene bridge, which may be optionally mono- or di-substituted by $C_1$-$C_5$-alkyl; or $R_3$ denotes a group of the formula

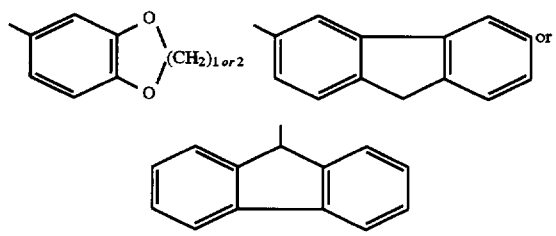

or $R_3$ denotes a group of the formula,

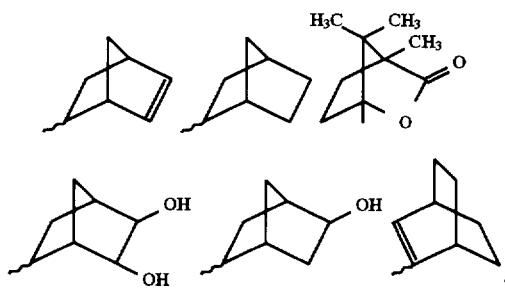

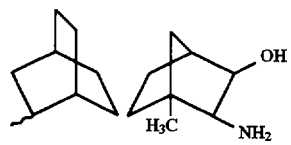

or adamantane; or $R_3$ denotes $C_3$-$C_7$-cycloalkyl, which is optionally substituted by $=O$, $-OH$, $-OR_8$, or $R_3$ denotes phenyl, which is optionally substituted by $-OH$, halogen, $-OR_8$, $C_1$-$C_4$-alkyl, $-NH_2$, $-COOH$, $-SO_3H$, $-COOH$, $-OCH_2COOH$, or $R_3$ denotes a norbornane, norbornene, a $C_3$-$C_6$ dicycloalkylmethyl or noradamantane group; or $R_3$ denotes $-CH=CH$-phenyl, the phenyl ring being mono- or poly-substituted by methoxy, hydroxy or halogen; or $R_3$ denotes a [3.3.0]-bicyclooctan-; a [3.3.0]-bicyclooctan-2-yl, or $R_3$ denotes a C-linked piperidine or furan;

$R_4$ denotes hydrogen, methyl or benzyl, wherein the benzyl group may be substituted by 1 to 3 methoxy groups; $CH_3-O-CH_2-$, $CH_3-S-CH_2-$,

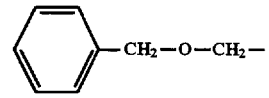

or, $-CH_2-CH=CH_2$;

$R_5$ denotes $C_1$-$C_4$-alkyl, which is optionally substituted by OH, $NH_2$ or $NR_6R_7$;

$R_6$ denotes hydrogen, a cycloalkyl group having 3 to 6 carbon atoms, a branched or unbranched alkyl, alkenyl or alkynyl group having up to 10 carbon atoms, which may be optionally substituted by hydroxy, phenyl, amino or $C_1$ to $C_8$-alkoxy;

$R_7$ denotes hydrogen, a cycloalkyl group having 3 to 6 carbon atoms, a branched or unbranched alkyl, alkenyl or alkynyl group having up to 10 carbon atoms, which may be optionally substituted by hydroxy, phenyl, amino or $C_1$ to $C_8$-alkoxy;

or $R_6$ and $R_7$ together with the nitrogen atom form a saturated or unsaturated 5 or 6 ring, which may contain nitrogen, oxygen or sulphur as an additional hetero atom, wherein the heterocyclic ring may be substituted by a branched or unbranched alkyl group having 1 to 4 carbon atoms, or may carry one of the following groups:

$-(CH_2)_n-NH_2$, $=O$, $-(CH_2)_nNH-C_1-C_4$-alkyl, $-(CH_2)_n-N(C_1-C_8$-alkyl$)_2$, halogen, $-OR_8$, $-NO_2$, $-NH_2$, $-CH_2NR_6R_7$, $-OH$, $-COOH$, $-SO_3H$, $-SO_2-R_8$, $R_8$ denotes hydrogen, $C_1$-$C_4$-alkyl, $C_2$-$C_4$-alkenyl, $C_2$-$C_4$-alkynyl, benzyl or phenyl group, which is optionally substituted once or several times by $OCH_3$;

$R_9$ denotes $C_1$-$C_4$-alkyl, $C_2$-$C_4$-alkenyl, $C_2$-$C_4$-alkynyl, phenyl, benzyl, $C_3$-$C_6$-cycloalkyl;

$R_{10}$ denotes $-COOH$, $-CH_2OR_8$, hydrogen, $C_1$-$C_3$-alkyl, phenyl, $-CH_2NR_6R_7$;

$R_{11}$ denotes hydrogen, phenyl, $-CH_3$, characterised in that a uracil derivative of the formula A or B

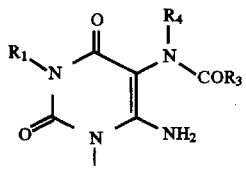

or

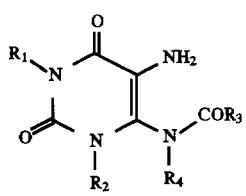

wherein $R_1$, $R_2$, $R_3$ and $R_4$ have the aforementioned meaning is dissolved in a suitable organic-aqueous solvent and cyclised in the presence of LiOH.

3. The process for preparing xanthine derivatives according to claim 2, by cyclising uracil derivatives A or B, wherein $R_1$ denotes hydrogen, $C_1$–$C_3$-alkyl, $C_3$–$C_4$-alkenyl, or $C_3$–$C_4$ alkynyl;

$R_2$ denotes hydrogen, a $C_1$–$C_3$-alkyl, $C_3$–$C_4$-alkenyl, or $C_3$–$C_4$-alkynyl group.

4. The process for preparing xanthine derivatives according to claim 3 or 2, by cyclising uracil derivatives A or B, wherein $R_3$ denotes a cyclopentane radical protected by a ketal group, wherein $R_1$, $R_2$ and $R_4$ are defined as before, and $R_3$ denotes a group from the group

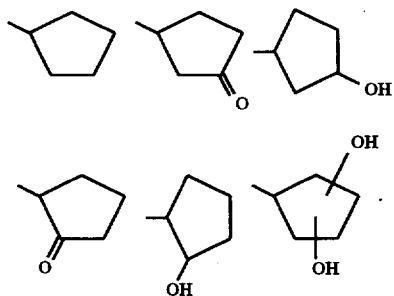

5. A process for preparing 1,3-dipropyl-8-(3-oxocyclopentyl) xanthine, characterised in that:

(a) 2-carboxy-8,8-dimethyl-6,10-dioxaspiro[4,5]decane is reacted with 1,3-dipropyl-5,6-diaminouracil to produce an amide of formula VI:

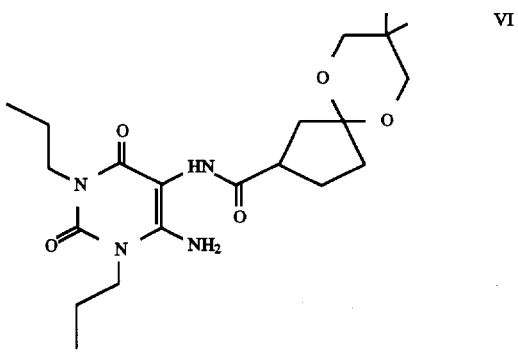

(b) the amide of formula VI is cyclised in a suitable solvent in the presence of LiOH/$H_2O$ to produce a ketal of formula VII:

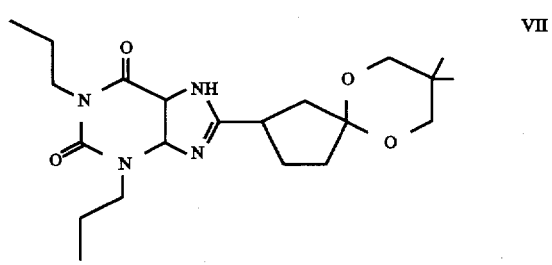

and (c) the ketal of formula VII is contacted with acid to produce 1,3-dipropyl-8-(3-oxocyclopentyl) xanthine:

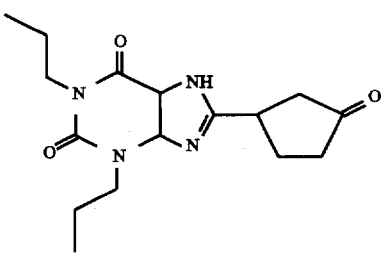

6. The process for preparing racemic or enantiomerically pure 1,3-dipropyl-8-(3-oxocyclopentyl)-xanthine according to claim 5, characterised in that enantiomerically pure 2-carboxy-8,8-dimethyl-6,10-dioxaspiro[4,5]decane is used.

* * * * *